(12) United States Patent
Bettenhausen et al.

(10) Patent No.: US 8,162,138 B2
(45) Date of Patent: Apr. 24, 2012

(54) UNIVERSAL SURGICAL FASTENER STERILIZATION CADDY

(75) Inventors: Cary A. Bettenhausen, Speedway, IN (US); Todd E. Bettenhausen, Indianapolis, IN (US); Thomas A. Deal, Indianapolis, IN (US)

(73) Assignee: ContainMed, Inc., Speedway, IN (US)

( * ) Notice: Subject to any disclaimer, the term of this patent is extended or adjusted under 35 U.S.C. 154(b) by 345 days.

(21) Appl. No.: 12/615,020

(22) Filed: Nov. 9, 2009

(65) Prior Publication Data

US 2011/0108446 A1    May 12, 2011

(51) Int. Cl.
    *B65D 85/24*    (2006.01)
(52) U.S. Cl. .................................... 206/339; 206/438
(58) Field of Classification Search ................ 206/339, 206/438, 341, 347, 346, 343, 211, 365
See application file for complete search history.

(56) References Cited

U.S. PATENT DOCUMENTS

| | | | | |
|---|---|---|---|---|
| 1,650,980 A | * | 11/1927 | Campbell | 206/366 |
| 4,955,476 A | * | 9/1990 | Nakata et al. | 206/346 |
| 5,098,676 A | | 3/1992 | Brooks, Jr. | |
| 5,259,501 A | * | 11/1993 | Withers et al. | 206/366 |
| 5,372,252 A | * | 12/1994 | Alexander | 206/210 |
| 5,518,115 A | | 5/1996 | Latulippe | |
| 5,850,917 A | * | 12/1998 | Denton et al. | 206/366 |
| 5,881,878 A | * | 3/1999 | Faccioli et al. | 206/438 |
| 5,975,295 A | * | 11/1999 | Diamond | 206/366 |
| 6,585,942 B1 | * | 7/2003 | Bussell et al. | 422/300 |
| 7,066,329 B2 | * | 6/2006 | Riley | 206/443 |
| 7,350,643 B2 | * | 4/2008 | Capanni et al. | 206/370 |
| 7,650,991 B2 | * | 1/2010 | Hester et al. | 206/339 |
| 2006/0006087 A1 | * | 1/2006 | Lin | 206/347 |
| 2008/0230423 A1 | * | 9/2008 | Loeffler et al. | 206/438 |

* cited by examiner

*Primary Examiner* — J. Gregory Pickett
*Assistant Examiner* — Ernesto Grano

(57) ABSTRACT

A universal surgical screw caddy. An enclosure includes a cover secured to a frame. A flexible sheet is located between an affixed to the cover and frame. A plurality of holes formed in the cover allow the surgical screws to be inserted into the caddy past a plurality of movable portions of the flexible sheet releasably holding the screws in the caddy.

19 Claims, 3 Drawing Sheets

UNIVERSAL SURGICAL FASTENER STERILIZATION CADDY

BACKGROUND OF THE INVENTION

1. Field of the Invention

The present invention relates generally to the field of surgical screw racks.

2. Description of the Prior Art

Surgical fasteners, such as surgical screws, must be sterilized, stored and be convenient for use during surgery. A variety of surgical screw racks have been devised having a plurality of holes into which a separate surgical screw is removably positioned. The racks may include covers movably mounted thereto to prevent a sterilized screw from accidentally falling from the rack. The covers may be slidably or hingedly mounted to the rack. In the event the rack is dropped, the screws might become dislodged thereby requiring complete re-sterilization.

Disclosed herein is a caddy for removably holding a plurality of surgical fasteners. The caddy does not include a movable cover to hold the fasteners and thus the screws are more accessible and convenient for use during surgery. Further, the shanks of the fasteners are positioned within the caddy whereas the fastener heads protrude above the caddy allowing for easy grasping to pull the particular fastener from the caddy. The caddy with mounted screws may be inserted directly into sterilization without requiring a separate container. Conventional fabric may be wrapped around the caddy for the sterilization.

Internal passages within the caddy allow for the sterilization fluid that enters the caddy to readily exit the caddy providing for a dry and sterile fastener. In the event the caddy disclosed herein is accidentally dropped, the fasteners are still held within the caddy by a plurality of releasable flaps.

SUMMARY OF THE INVENTION

One embodiment of the present invention is the combination of a plurality of surgical fasteners and a fastener caddy for holding the fasteners during sterilization and thereafter as the fasteners are removed, one at a time, from the caddy for use in surgery. The caddy includes a plurality of internal passages provided in the caddy frame. A flexible sheet, with movable flaps, is mounted to the caddy frame by a rigid sheet. The rigid sheet has a plurality of holes aligned with the flaps and passages. The flaps are moved into the passages by the fastener shanks as they are extended into the passages being held therein by the flaps.

DESCRIPTION OF THE PREFERRED EMBODIMENTS

Figure 1:
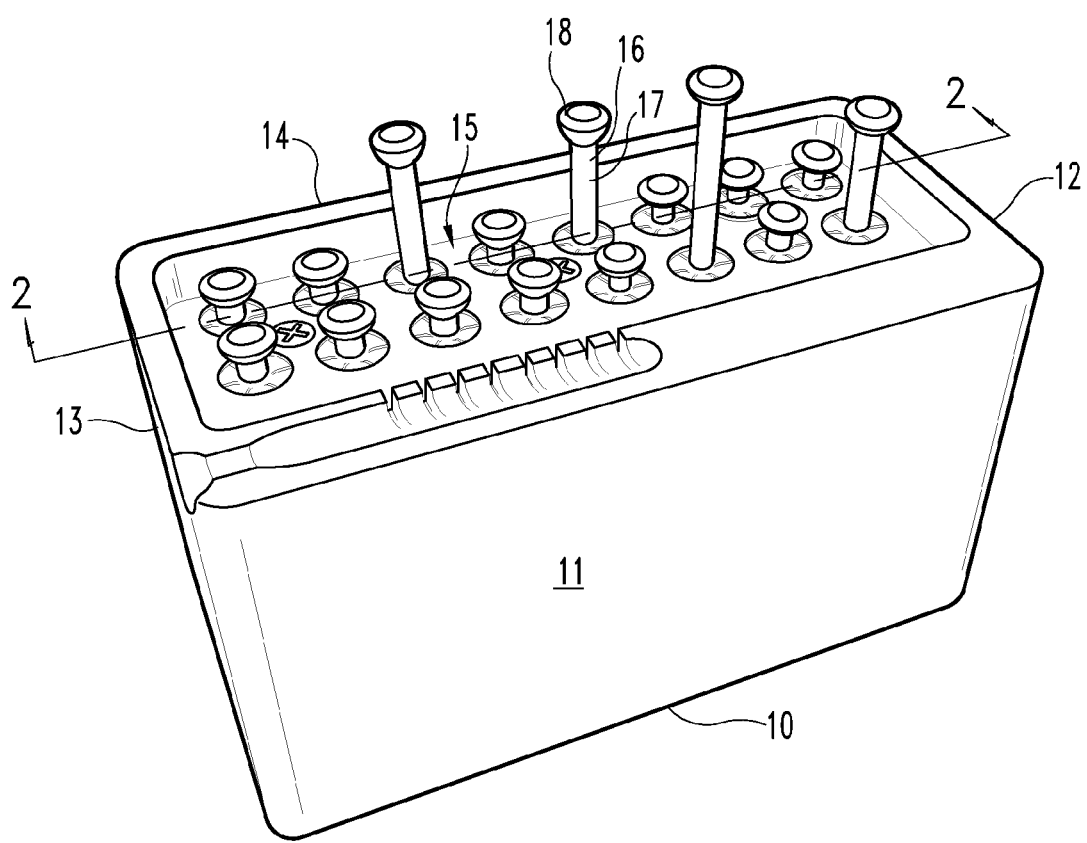
FIG. 1 is a perspective view of the preferred embodiment of a surgical caddy having a plurality of surgical screws removably mounted thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
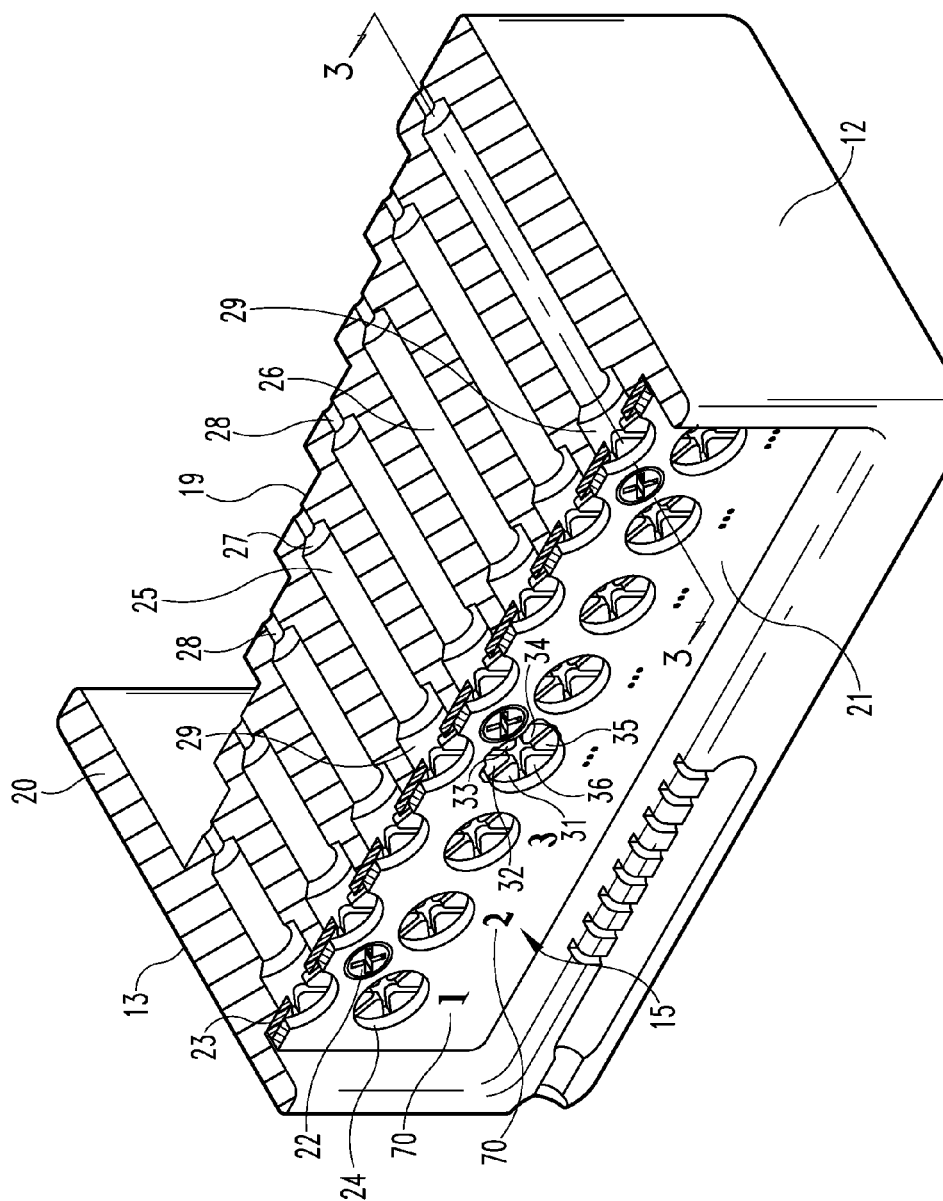
FIG. 2 is a cross-sectional view taken along a line of FIG. 1 and viewed in the direction of the 2-2 arrows with the surgical screws removed from the caddy.
Figure 3:
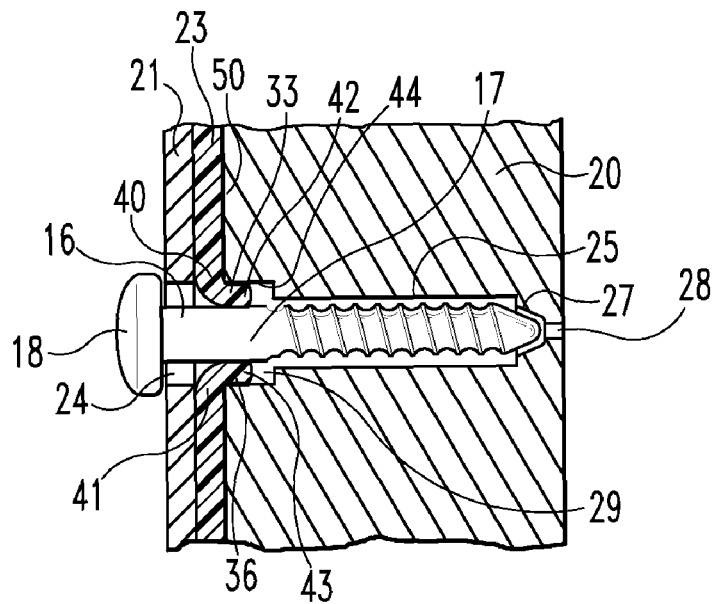
FIG. 3 is a cross-sectional view taken along a line of FIG. 2 and viewed in the direction of the 3-3 arrows showing one of the surgical screws located within one of the caddy passages.

Referring now more particularly to FIGS. 1-3, there is shown a preferred embodiment of a universal surgical fastener caddy to hold surgical fasteners or screws during the sterilization thereof and also when subsequently used during surgery. The caddy 10 includes a box like enclosure having a pair of end walls 12 and 13 joined to side walls 11 and 14. The top end 15 includes a plurality of holes through which the surgical fasteners or screws 16 may be inserted. Surgical screws 16 are commercially available and include a shank 17 having an outside diameter integrally joined to a head 18 also having an outside diameter. A variety of surgical screws are commercially available having a variety of configurations. For example, the shank may have external threads extending along a portion or the entire length of the shank. Likewise, the shanks and heads may be hollow.

A cross-sectional view of the caddy is shown in FIG. 2 without the surgical screws being inserted therein to more clearly illustrate the construction. In the embodiment of FIG. 2, the frame 20 is in a block configuration and consists of the end walls 12 and 13 integrally joined to the side walls 11 and 14. The bottom 19 of frame 20 may extend between end walls 12 and 13 in a single plane or may be graduated, such as shown in FIG. 2, and extend in a variety of parallel planes to accommodate different lengths of surgical screws.

Frame 20 has an open top 15 that is closed by a rigid cover 21 fixedly secured to frame 20 by a plurality of conventional fasteners 22 extending into the frame. A flexible sheet 23 is parallel to cover 21 and is positioned between frame 20 and cover 21 being held to the frame by fasteners 22. Fasteners 22 have shanks extending through cover 21 and flexible sheet 23 and then threadedly received by frame 20. The head of fastener 22 abuts against the cover 21 thereby securing the cover, sheet and frame together.

Cover 21 is rigid and includes a plurality of screw holes 24 arranged in rows and aligned with passages 25 provided in the main body of frame 20 which are also arranged in rows. Passage 25 will now be described it being understood that an identical description applies to the remaining passages. Passage 25 has a circular cross-section that tapers down at bottom end 27 emptying into a drain hole 28 leading to external of the frame. The top end of passage 25 includes a counter bore portion 29 immediately beneath a hole 24. Typically, the inside diameter of the counter bore portion 29 is the same as the inside diameter of hole 24; however, the present invention includes having a inside diameter of counter bore portion 29 different from the inside diameter of hole 24.

Flexible sheet 23 includes a plurality of flaps or movable portions positioned between each hole 24 and its associated passage 25. In the embodiment shown in FIG. 2, flexible sheet 23 includes six such movable flaps positioned adjacent each hole 24. It is to be understood that the present invention includes more than or less than six movable flaps positioned adjacent each hole 24. As an example, movable flaps 31, 32, 33, 34, 35 and 36 are shown for each hole 24. Each movable flap has a proximal end integrally joined to sheet 23 and a free movable distal end located adjacent the longitudinal axis that extends through hole 24 and passage 25. As a surgical screw is inserted through a hole, the shank of the screw contacts the movable flap thereby forcing the movable flap into a counter bore portion 29 with the shank then extending further into the reduced cylindrical portion 26 of the passage 25 until the tip of the screw contacts the tapered end 27 of the passage that provides a stop surface limiting further extension of the screw into the passage. The depth of the counter bore portion 29 must be deep enough to prevent interference with the tips of the flaps.

As shown in FIG. 2, the passages 25 may have different lengths depending upon the length of the particular surgical screw to be inserted therein. The length of passage 25 is less than the length of the screw shank to be inserted therein so that the bottom end of the screw may contact tapered end 27 while always positioning the head of the screw above cover 21 enabling the user to quickly grasp the head 18 of the surgical screw during surgery.

FIG. 3 illustrates a surgical screw 16 inserted into the caddy. The shank 17 of the screw has been inserted through hole 24 contacting the movable flaps of flexible sheet 23 forcing the movable flaps into counter bore 29 while the shank of the screw extends downwardly with the bottom end of the screw contacting the stop surfaces formed by the tapered passage end 27. Instead of forming a tapered passage end 27 to form the stop surfaces contacted by the tip of shank 17, the present invention contemplates and includes using a flat wall, a counter drilled wall, a counter bored wall, or an angled wall to form the stop surfaces leading to or not leading to the drain hole 28 or even not using a wall at all with stop surfaces. The size of counter bore 29 is selected so that the movable flaps are forced against the internal surface of the counter bore 29 by the screw, thereby allowing deflection of the flaps within the counter bore. The distal ends of the flaps are spaced apart a distance less than the diameter of the fastener shank inserted therebetween. Thus, the flaps deflect into the caddy as the fastener shank is inserted and deflected out of the caddy as the fastener shank is pulled from the caddy. As the fastener shank is pulled outwardly and the flaps move from between being deflected inwardly to outwardly relative to the caddy, the flaps will move to a plane generally parallel to the main body of the flexible sheet thereby becoming compressed since the distal ends of the flaps are spaced apart less than the diameter of the shank. Thus, if the caddy is dropped or turned upside down, the screw will not fall from the caddy. On the other hand, the head 18 of the screw is positioned outwardly of cover 21 and may be grasped thereby allowing the user to pull the surgical screw from the caddy.

FIG. 3 illustrates a cross-section of two of the movable portions or flaps 33 and 36 having proximal ends 40 and 41 integrally attached to the flexible sheet whereas the flap distal ends 42 and 43 are free to move into and out of the counter bore. A stop surface 44 is formed by the inside surface of the counter bore allowing the flaps to be deflected as the shank is moved through the counter bore.

During the sterilization of the caddy loaded with surgical screws, the sterilization fluid may enter through hole 24 passing between the flaps and down into passage 25, eventually exiting passage 25 via drain hole 28.

The movable flaps immediately adjacent each hole 24 are arranged to define a hole through the flexible sheet 23 through which the shanks of the surgical screws may be extended with the flaps engageable with the shanks to removably hold the shanks but releasable to enable the user to pull the sterilized screw from the caddy. Cover 21 and the top 50 of frame 20 are rigid in order to limit the movement of the flexible sheet as the surgical screws are inserted and pulled from the caddy. Cover 21 prevents flexible sheet 23 from moving apart from the main body as the screws are pulled from the caddy while allowing the movable flaps to move back to their normal position extending across each passage. On the other hand, the rigid top 50 of frame 20 provides a solid surface limiting movement of the flexible sheet except at the point of the movable flaps as the surgical screws are inserted into each passage.

The counter bore shaped portion include the continuous internal surfaces 44 thereby forming the first stop surfaces which continuously surround the screw shank as it is inserted into the passage. The inside diameter of counter bore 29 is chosen so when coupled with the thickness of the flaps extending into the counter bore in relationship to the outside diameter of the screw shank 17 allows the flaps to be deflected. On the other hand, the diameter of head 18 is sufficiently large as compared to the diameter of screw shank 17 so as to not extend into the counter bore portion being limited by the thickness of the flaps and the internal diameter of the counter bore in relationship to the diameter of the head 18 in the case a relatively short surgical screw is inserted into a relative long passage 25. In the event the proper length of screw is inserted into the proper length of passage, then the bottom tip of the screw contacts the stop surface formed by the tapered passage end 27 ensuring that the head of the screw remains external to the caddy.

The inside diameter of the reduced portion 26 of passage 25 is chosen to be slightly larger than the outside diameter of the screw shank to limit sideways movement of the surgical screw as it is inserted and held within the passage. The inside diameter of the passage is enlarged at the counter bore portion 29 to enable the flexible sheet flap to extend into the counter bore portion.

FIGS. 1-3 illustrate the frame 20 constructed in a block configuration with the passages 25 then being formed within the block construction. Nevertheless, it is contemplated and included that frame 20 may have a variety configurations.

Figure 4:
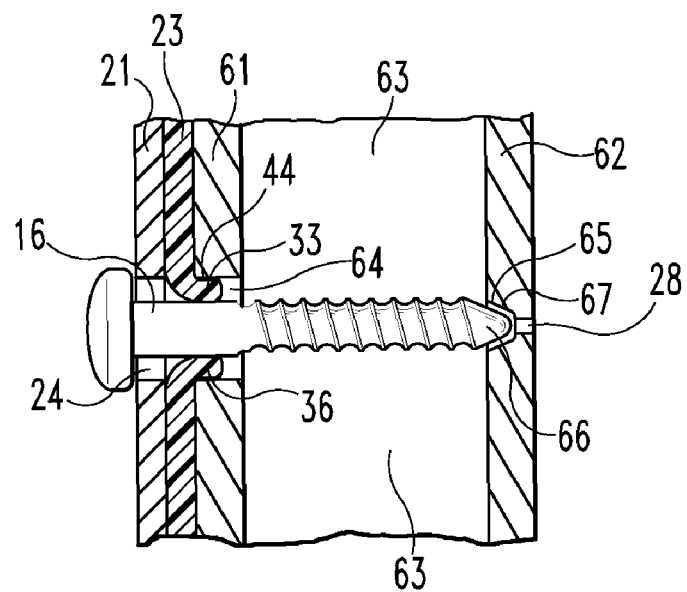
FIG. 4 is the same view as FIG. 3 only showing an alternate embodiment of the caddy.

For example, a surgical screw is shown inserted into an alternate embodiment of the caddy in FIG. 4. The alternate embodiment of FIG. 4 is identical to the preferred embodiment of FIGS. 1-3 with the exception that frame 20 is not constructed in block form but includes a pair of separate plates 61 and 62 spaced apart by gap 63. Thus, the rigid cover 21 is fixedly secured by fasteners 22 (FIG. 2) to rigid member 61 with flexible sheet 23 positioned between cover 21 and member 61. Fasteners 22 force cover 21 against flexible sheet 23, in turn, forced against plate 61.

Plate 61 has a hole 64 with the same diameter as counter bore 44 previously described and sized with respect to the moveable flaps. Thus, the shank of the surgical screw is extended through hole 24 of cover 21 forcing the movable flaps into hole 64 allowing the movable flaps to be deflected. The shank of the screw continues downwardly through gap 63 and is received in an upwardly opening recess 65 forming a tapered stop surface 67 aligned with drain hole 28. Thus, the tip 66 of the screw shank contacts the tapered stop surface 67 of recess 65 formed in plate 62. Plates 61 and 62 are connected together by the side walls 11 and 14 and end walls 12 and 13 (FIG. 1). Thus, the alternate embodiment of FIG. 4 is identical to the preferred embodiment with the exception that in the design of FIG. 4, a cylindrical passage does not extend between hole 64 and recess 65. Side ways movement of the screw shank is limited by the tip 66 of the shank being nested within recess 65. Plate 62 may extend in a single plane between end walls 12 and 13 providing reception of the same length of screws. Alternatively, a plurality of plates 62 may be connected together in step form in accordance with the bottom step configuration of frame 20 to accept different lengths of screws. Thus, the stop surfaces formed by an internal surface of recess 65 are located the distances from the flexible sheet 23 to position the surgical screws within the frame depending upon the length of the shank of the surgical screws in order to position the screw heads outwardly of cover 21.

In lieu of using the block configuration of FIG. 1-3 or the plate configuration of FIG. 4, the present invention includes using an entirely open design wherein one or more flexible sheets may be arranged atop one another forming a sandwich configuration to align and hold the surgical fasteners and allow the fasteners to be visible form the side of the caddy. In the sandwich configuration, the embodiment shown is FIG. 4 is modified slightly by replacing wall 62 with a pair of rigid walls between which is positioned a flexible wall all secured together and spaced apart from walls 21 and 61 and sheet 23. The flexible wall positioned between the pair of rigid walls may include flaps identical to those previously disclosed or may simply have a passage through which the fastener shank may pass.

The caddy shown in the drawings are particularly useful in combining with the plurality of surgical fasteners having shanks extended into the caddy. The fasteners may be removed one at a time from the caddy for use during surgery.

In order to indicate to the user the particular length of screw inserted into the caddy, indicia 70 is marked on the outward surface of cover 21 in a conventional fashion as is the custom with commercially available screw caddies.

The flexible sheet 21 is produced from silicone for both embodiments disclosed herein whereas cover 21, frame 20 and plates 61 and 62 are produced from a rigid material. Cover 21 is immovable and fixed to plate 61 by fasteners 22 or other conventional means.

The caddy disclosed herein will accept fastener shanks of different diameters within the same hole since the flaps will deflect as the shanks are inserted. The flaps might not return to a non-deflected condition when the shanks are pulled outwardly in the event the shanks are of sufficient large diameter relative to the spacing between the distal ends of the flaps. The flaps deflect ninety degrees into the caddy during shank insertion and remain deflected while holding the shank. The flaps reverse deflection when the shank is extracted from the caddy. On screws or implants with smooth sides or fine threads, the flaps may not need to reverse deflection.

The caddy may be utilized for holding not only surgical screws but also holding any type of cylindrical item, such as other implants including small rods or bone plates. Thus, it is to be understood that the term fastener used herein includes any type of cylindrical item including small rods or bone plates.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. The combination of:
    a plurality of surgical implants having cylindrical shanks with said implants each having a cylindrical shank;
    a surgical implant caddy for holding said surgical implants during sterilization thereof and thereafter as said implants are removed, one at a time, from said caddy for use in surgery; and wherein said caddy includes:
    a flexible sheet;
    a rigid sheet; and,
    a caddy frame having a top end with a plurality of passages each sized to receive a cylindrical shank, said rigid sheet extending over said top end and affixed thereto with said flexible sheet located between said rigid sheet and said top end of said frame, said flexible sheet having a plurality of movable flaps integrally joined thereto aligned with said passages and having a first position extending over said passages and a second position extending into said passages when said cylindrical shanks extend into said passages being removably held therein by said movable flaps, said movable flaps arranged in a group associated with each passage and said movable flaps in a group spaced apart a distance less than the diameter of said cylindrical shank limiting movement of said cylindrical shank.

2. The combination of claim 1 wherein:
said passages have a first cross section limiting sideways movement of said cylindrical shanks positioned therein and a larger cross section adjacent said flexible sheet allowing said cylindrical shanks to move said movable flaps.

3. The combination of claim 2 wherein:
said surgical implants are screws with threaded shanks and heads integral therewith, said passages are sized to allow insertion of said cylindrical shanks into said passages while preventing insertion of said heads therein.

4. The combination of claim 3 wherein:
said flexible sheet is silicone.

5. The combination of claim 3 wherein:
said frame has a bottom end with a plurality of drain holes leading to said passages allowing sterilization fluid to flow past said movable flaps and into said passages and then out of said passages via said drain holes.

6. The combination of claim 5 wherein:
said passages are arranged in different sizes to accommodate different sized surgical implants.

7. The combination of claim 6 wherein:
said rigid sheet is immovable and includes holes into which said cylindrical shanks extend with said holes aligned with said passages to allow grasping thereof as said cylindrical shanks are pulled outwardly from said passages.

8. The combination of claim 7 wherein:
said rigid sheet includes indicia associated with the different sized passages to indicate the size of screw to be inserted therein.

9. The combination of claim 1 wherein:
said top end of said caddy frame is rigid and positioned inwardly of said flexible sheet limiting inward movement of said flexible sheet when said cylindrical shanks are inserted in said caddy frame.

10. The combination of:
    a surgical implant with a cylindrical shank;
    a surgical implant caddy for holding said surgical implant during sterilization thereof and thereafter as said implant is removed from said caddy for use in surgery; and wherein said caddy includes:
    a flexible sheet;
    a rigid member; and,
    a caddy frame having a top end with a passage sized to receive said cylindrical shank, said rigid member positioned on said top end and affixed thereto with said flexible sheet located between said rigid member and said top end of said frame, said flexible sheet having a plurality of movable flaps integrally joined thereto and arranged in a group with said group of said movable flaps aligned with said passage, said movable flaps having a first position extending over said passage when said cylindrical shank is absent from said passage and a second position extending into said passage when said cylindrical shank extends into said passage and being removably held therein by said movable flaps engaging said shank, said cylindrical shank sized relative to said movable flaps to move said movable flaps from said first position to said second position as said cylindrical shank is inserted into said passage and to move said movable flaps back to said first position as said cylindrical shank is removed from said caddy.

11. The combination of claim 10 wherein:
said passage has a first cross section limiting sideways movement of said cylindrical shank positioned therein and a larger cross section adjacent said flexible sheet allowing said cylindrical shank to move said movable flaps.

12. The combination of claim 10 wherein:
said surgical implant is a screw with a threaded shank and head integral therewith, said passage is sized to allow insertion of said cylindrical shank into said passage while preventing insertion of said head therein.

13. The combination of claim 12 wherein:
said flexible sheet is silicone.

14. The combination of claim 12 wherein:
said frame has a bottom end with a drain hole leading to said passage allowing sterilization fluid to flow past said movable flaps and into said passage and then out of said passage via said drain hole.

15. The combination of claim 10 wherein:
said rigid member is immovable and includes a hole into which said cylindrical shank extends with said hole aligned with said passage to allow grasping thereof as said cylindrical shank is pulled outwardly from said passage.

16. The combination of claim 15 wherein:
said rigid member includes indicia associated with the passage to indicate the size of screw to be inserted therein.

17. The combination of claim 10 wherein:
said top end of said caddy frame is rigid and positioned inwardly of said flexible sheet limiting inward movement of said flexible sheet when said cylindrical shank is inserted in said caddy frame.

18. A caddy in combination with surgical fasteners comprising:
a plurality of surgical fasteners with cylindrical shafts;
a housing with passages to receive said cylindrical shafts;
a rigid component mounted to said housing with said rigid component having holes aligned with said passages allowing said surgical fasteners to extend through said holes and into said passages;
a plurality of movable portions mounted to said housing, said movable portions are arranged in groups with a separate one of said groups extending over a separate one of said passages, said movable portions in said groups having proximal ends fixed to said housing and freely movable distal end portions that are deflected in said passages to engage and removably hold said cylindrical shafts in said passages but yieldable to allow said cylindrical shafts to be pulled outwardly from said housing; and, wherein:
said plurality of movable portions are in the form of a flexible sheet located between said rigid component and said housing; and,
said surgical fasteners have enlarged heads relative to said cylindrical shafts with said holes of said rigid component being smaller than said heads limiting movement of said heads through said holes.

19. The caddy in combination with surgical fasteners of claim 18 wherein said housing has a rigid sheet with said passages extending there through, said flexible sheet is located between said rigid component and said rigid sheet, said passages in said rigid sheet sized to allow said cylindrical shafts to extend there through while said movable distal end portions are deflected into said passages in said rigid sheet engaging said cylindrical shafts and removably holding said cylindrical shafts in said housing.

* * * * *